United States Patent [19]
Fletcher

[11] Patent Number: 6,050,998
[45] Date of Patent: Apr. 18, 2000

[54] BONE FASTENER

[75] Inventor: Stephen A. Fletcher, 8830 Long Point, Suite 706, Houston, Tex. 77005

[73] Assignee: Stephen A. Fletcher, Houston, Tex.

[21] Appl. No.: 09/316,927

[22] Filed: May 21, 1999

[51] Int. Cl.$^7$ ............................................. A61B 17/56
[52] U.S. Cl. ........................ 606/74; 606/232; 606/103
[58] Field of Search ............................. 626/61, 72, 73, 626/74, 232, 103

[56] References Cited

U.S. PATENT DOCUMENTS

| | | | |
|---|---|---|---|
| 3,111,945 | 11/1963 | Solbrig | 606/74 |
| 3,570,497 | 3/1971 | Lemole | 606/74 |
| 4,119,091 | 10/1978 | Partridge | 606/74 |
| 5,571,105 | 11/1996 | Gundolf | 606/72 |
| 5,683,404 | 11/1997 | Johnson | 606/74 |
| 5,725,582 | 3/1998 | Bevan et al. | 606/61 |
| 5,772,663 | 6/1998 | Whiteside et al. | 606/74 |
| 5,908,421 | 6/1999 | Beger | 606/61 |

*Primary Examiner*—Michael Buiz
*Assistant Examiner*—Daphna Shai
*Attorney, Agent, or Firm*—Trop, Pruner & Hu, P.C.

[57] ABSTRACT

A bone fastener includes a strand which may be threaded through drilled passages in separate but adjacent bone sections such that the ends of the fastener may be quick connected to one another. For example, one end of the fastener may be threaded through an aperture in the other end such that a self-locking and adjustably tensionable connection is achieved. In addition, a burr hole plate may be secured over a burr hole by threading the fastener through a connector on the burr hole plate and securing the fastener to the bone sections.

5 Claims, 5 Drawing Sheets

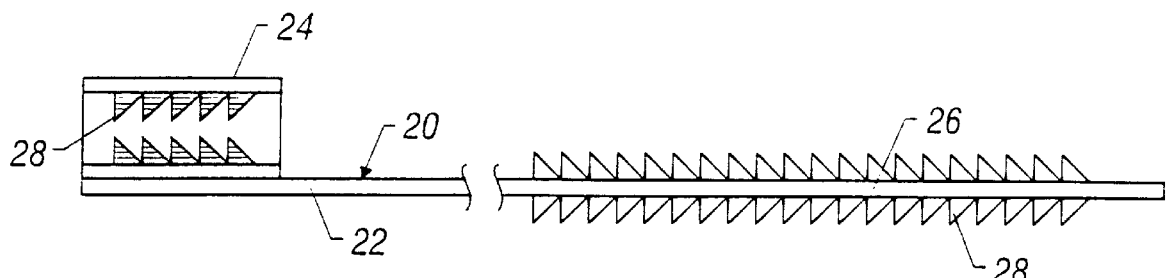
Figure 1
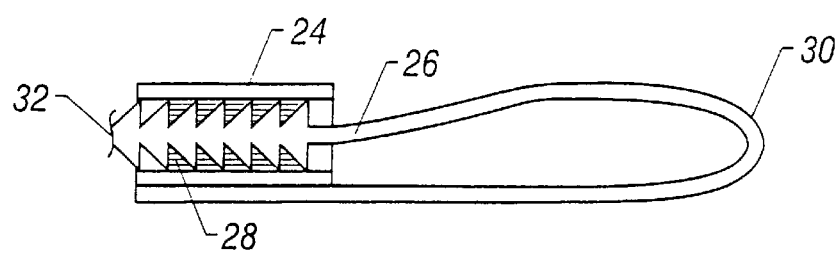
Figure 2
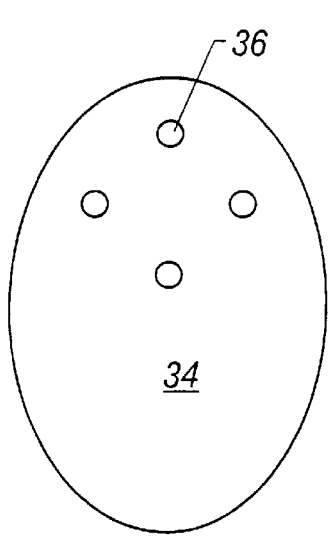 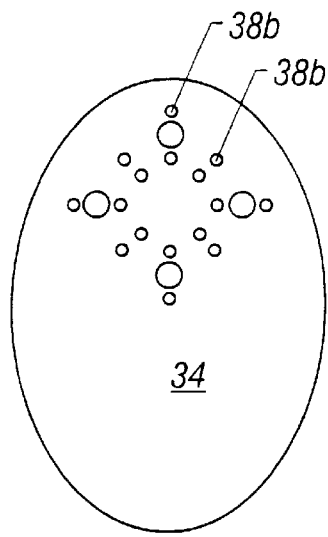
Figure 3      Figure 4

BONE FASTENER

This invention relates generally to fasteners used to connect sections of bone in the course of surgical procedures and particularly to surgical wires adapted to facilitate wire end connections.

BACKGROUND

Surgical wires are utilized to connect a variety of bone sections in the course of surgical procedures. For example, surgical wires are used in craniotomies wherein a portion of the skull, called a skull flap, is completely removed from the skull to allow access to the brain. The skull flap is secured to the skull after the operation is completed using surgical wire which is threaded through several pairs of drilled holes, one on each side of each saw cut that formed the skull flap. Ends of the wire are twisted together and the excess wire is cut off. The twisted together wire ends are then stuffed into an enlarged or countersunk opening formed in one of the drilled holes. Thus, the wire connection does not penetrate the skin after the skin is replaced over the skull flap.

Initially, the removal of the skull flap begins by drilling a set of holes, usually four holes, called burr holes, at spaced locations, defining the corners of the skull flap. Each pair of adjacent holes are utilized to define the ends of a saw cut. Where four burr holes are utilized, four saw cuts connecting the holes are utilized to remove the skull flap from the rest of the skull.

Since the burr holes tend to be of a substantial diameter, it is necessary to cover these holes at the conclusion of the operation. This is normally done using a plate which is positioned over each burr hole. The plates are secured to the skull using a plurality of threaded fasteners distributed around the periphery of the plate.

While all these techniques have been utilized for a number of years without substantial variation, these techniques have some disadvantages. The use of wire sections whose ends are then wrapped together to create the connection tends to be time consuming. In all surgical operations it is desirable to complete the operation as quickly as possible to reduce cost and, more importantly, to minimize the amount of time that the internal tissues are exposed to the atmosphere.

Similarly, the use of burr hole covering plates with threaded fasteners tends to be time consuming and expensive. In addition, the surgical facility may need to have an inventory of such plates and fasteners to accommodate a variety of different situations. This adds to overhead and ultimately to patient expense.

It would be desirable to have an equally effective technique for securing bone portions to other bone portions which is easier, quicker and more economical than existing techniques.

SUMMARY

Bone sections, such as a skull flap formed in a craniotomy, can be connected using fasteners having end connectors. For example, end connectors may be connected by threading one end connector through an opposite end connector to form a loop. The loop is then pulled tight to securely connect two bone sections without any twisting or coiling of wire ends. As a result, in a simple self-locking threading motion, the connections can be made up and tightened as desired.

In accordance with one embodiment, a bone fastener includes a strand of material compatible with human tissue. The strand includes a pair of opposed portions. A first connector is located on one portion and a second connector is located on the other portion. The first and second connectors are adapted to connect the portions when the first portion is threaded through the second portion.

BRIEF DESCRIPTION OF THE DRAWING

FIG. 1 is a partially cut-away cross-sectional view through one embodiment of the present invention;

FIG. 2 is a cross-sectional view of the embodiment shown in FIG. 1 after the two connector ends have been connected together;

FIG. 3 is a top plan view of an exposed skull showing the formation of typical pattern of burr holes;

FIG. 4 is a top plan view of the embodiment shown in FIG. 3 after additional wire holes have been formed in connection with the previously formed burr holes;

DETAILED DESCRIPTION

Figure 5:
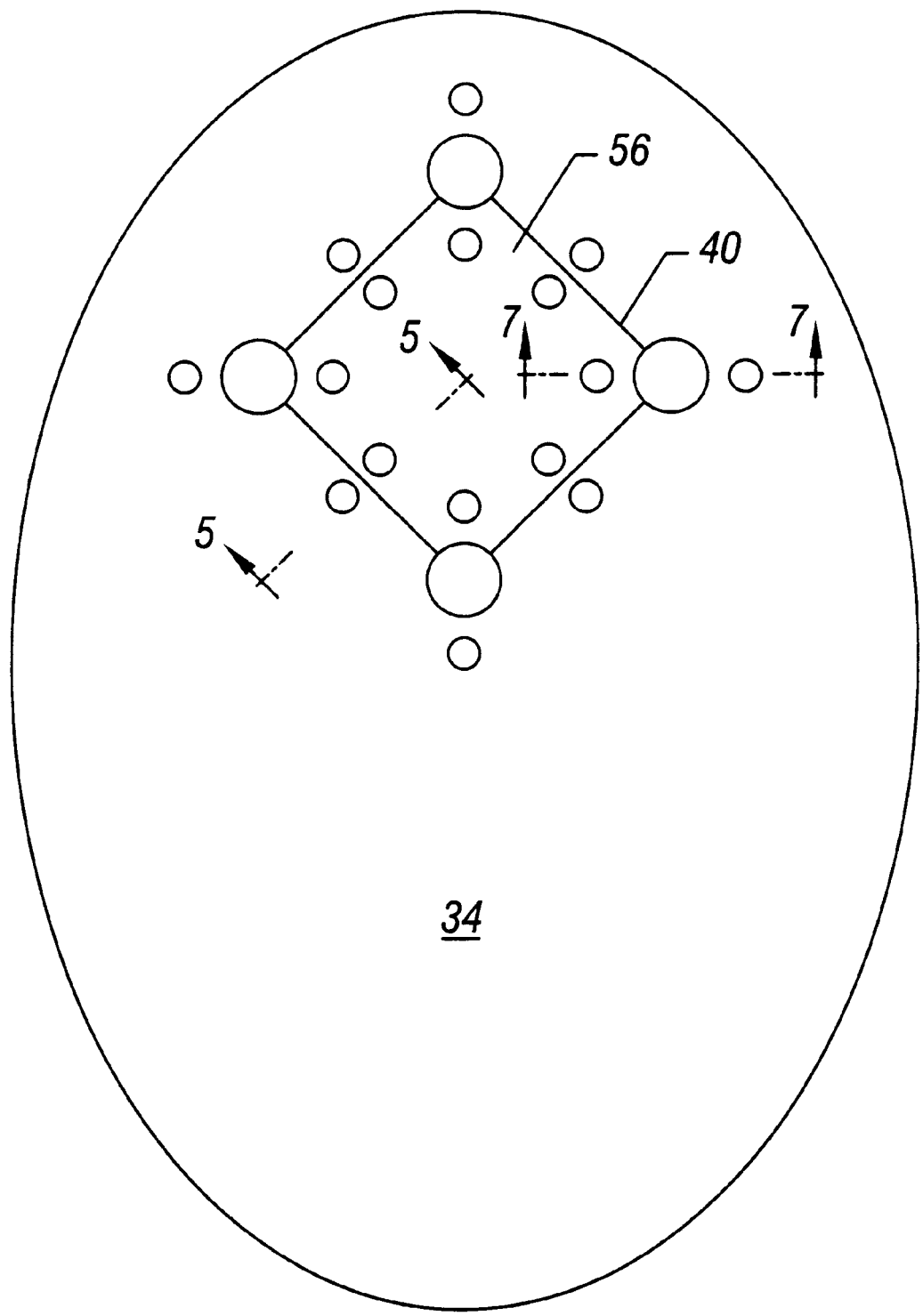
FIG. 5 is a top plan view of the embodiment shown in FIG. 4 after saw cuts have been formed between adjacent burr holes.

Referring to the drawing wherein like reference characters are used for like parts throughout the several views, a bone fastener 20, shown in FIG. 1, includes a strand 22 and a pair of connector portions 24 and 26 on opposed ends of the strand 22. The strand 22 is conventionally made of surgical steel or other metals known to be suitably compatible with human body tissue. However, plastic materials could be utilized as well.

A variety of strand sizes may be utilized in terms of both length and diameter depending on the application. In connection with craniotomies, conventional craniotomy wire diameters may be utilized and strand 22 lengths of, for example, 6 or 8 inches, may be suitable. While the portions 24 and 26 are illustrated as being integrated with the strand 22, either of both of the portions 24 or 26 may be secured to the strand 22 by welding, crimping or other known connection techniques.

Other bone fastening applications of the present invention, in addition to craniotomy applications, include spinal fusion surgery, and jaw surgery such as maxillary fixation and the attachment of arch bars.

The connector portion 26 may include a plurality of barbs 28 located around its periphery. The barbs may be single, discrete barbs which are randomly distributed about the end portion 26. The barbs may also be ring-like sections serially spaced from one another along the length of the portion 26. The end 27 of the strand 22 may be pointed to facilitate connection between the portions 24 and 26.

The connector portion 24 may include a tubular socket 25 with one or more internal barbs 28. The barbs 28 in the socket 24 may correspond generally to the barbs 28 on the portion 26 but may be directed generally at an opposite angulation to that of the opposing barbs on the portion 26 to facilitate a self-locking connection as illustrated in FIG. 2. The portions 24 and 26 may be turned on one another to form a loop 30. The barbs 28 of the portion 26 may then engage the barbs 28 of the socket 24. Because of the opposed angulation of the barbs on the respective portions, it is difficult or impossible to withdraw the portion 26 once it has been threaded through the socket 24. Thus, the connection is adjustable in terms of the length of the loop 30 and self-locking. After the desired length of loop 30 is formed, the excess length of the portion 26 may be removed as indicated at 32.

The application of the fastener 20 to a craniotomy is illustrated in FIGS. 3–6 and 14. As shown in FIG. 3, the exposed skull 34 has a set of four burr holes 36 formed therein, for example, in a trapezoidal pattern. After the burr holes 36 have been formed, a plurality of smaller diameter wire holes 38a and 38b may be formed. Each pair of wire holes 38a may be positioned along the line connecting adjacent burr holes 36 and arranged to transversely thereto. The wire holes 38b may be positioned on outward and inward edges of the burr holes 36 but are spaced slightly therefrom.

Figure 6A:
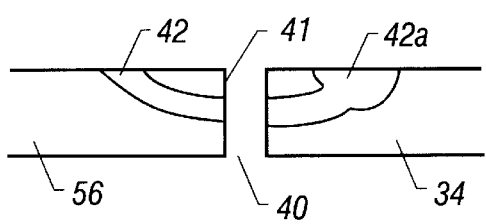
FIG. 6a is a partial, enlarged cross-sectional view taken generally along the line 5—5 in FIG. 5.

As shown in FIG. 5, saw cuts 40 are then formed between adjacent burr holes 36, bisecting the opposed pairs of wire holes 38a. As shown in FIG. 6a, the holes 38a may or may not be formed at an angle exiting through a bone section side surface 41. One of the passages 42a connected to each pair of holes 38a is formed with an enlarged or countersunk opening at the upper surface 34a of the skull 34. A passage 42 of each pair of passages 42, 42a need not include a countersunk region.

Figure 6B:
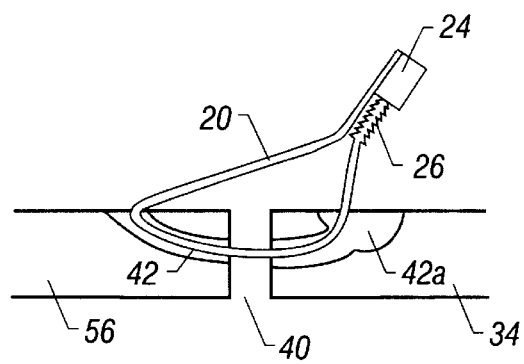
FIG. 6b is a partial, enlarged cross-sectional view corresponding to FIG. 6a after a wire has been threaded through the drill holes.
Figure 6C:
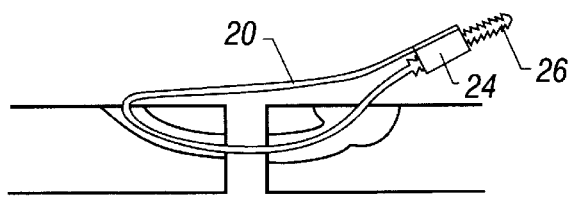
FIG. 6c is a partial, enlarged cross-sectional view corresponding to FIG. 6b after the wire ends have been made up.
Figure 6D:
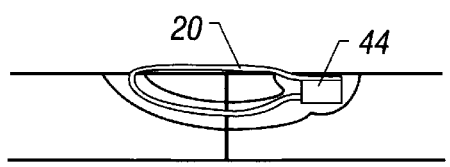
FIG. 6d is a partial, enlarged cross-sectional view corresponding to FIG. 6c after the wire ends have been made up and stuffed into an enlarged opening formed on an upper surface of the skull.

The skull flap 56, best shown in FIG. 14, is secured to the remainder of the skull 34 by threading fasteners 20 through the drill passages 42 and 42a of adjacent pairs of wire holes 38a as illustrated in FIG. 6b. Then, as shown in FIG. 6c, the portion 26 is threaded through the socket 24 of the fastener 20 to form an adjustable, sliding, self-locking connection between those portions. Because of the arrangement of the barbs 28, the connection portion 26 can be slid through the socket 24 to the extent desired but cannot be backed out therefrom. When the desired tightness has been achieved between the skull flap and the remainder of the skull, the excess fastener portion 45 is simply cut away. The portion 24 is pushed into the countersunk passage 42a, as shown in FIG. 6d. This prevents the portion 24 from protruding through the skin (not shown) after the skin is replaced over the skull.

Figure 7:
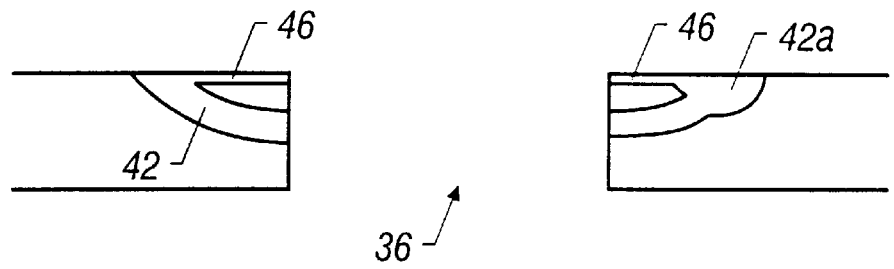
FIG. 7 is a partial, enlarged cross-sectional view taken generally along the line 7—7 in FIG. 5.

The formation of the wire holes 38b, shown in FIG. 7, also includes a first angled drill passage 42 along one edge of the skull flap 56 and a second angled passage 42a with a countersunk adjacent the upper surface 34a of the skull 34. In addition, a groove 46 may be formed in each skull section to receive the strand 22 so that the top of the strand 22 is level with the upper surface 34a of the skull.

Figure 8:
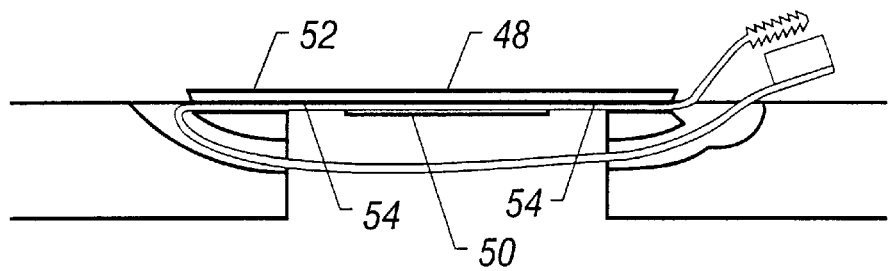
FIG. 8 is a partial, enlarged cross-sectional view corresponding to FIG. 7 after a fastener has been inserted.
Figure 9:
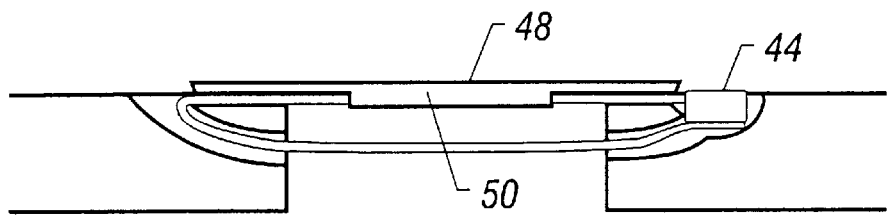
FIG. 9 is a partial, enlarged cross-sectional view corresponding to FIG. 8 after the wire connection has been made up.
Figure 10:
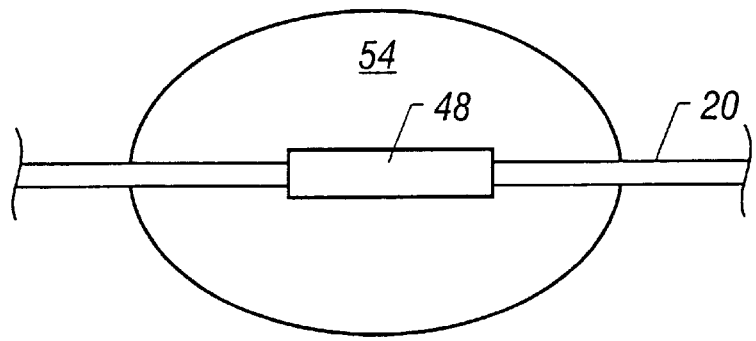
FIG. 10 is a bottom plan view of a burr hole plate in accordance with one embodiment of the present invention.

A burr hole plate 48 may cover a burr hole 36, overlapping the adjacent skull regions. The plate 48 may be formed of any material compatible with human tissue including surgical steel, metals and possibly plastics as well. As shown in FIGS. 8 to 10, an upper side 52 of the plate 48 is either generally flat or may be curved to conform to the skull curvature and the lower side 54 includes a tube 48 which guides the fastener 20. With the plate 48 positioned over the burr hole 36, the fastener 20 may be fed through the drill passages 42, 42a and through the tube 50 on underside 54 of the plate 48. The fastener 20 may then be tightened as described previously. After the fastener has been fed through the socket 24, the fastener 20 may be cut off at the socket 24, as illustrated in FIG. 9. The socket 24 and any extra strand material is then pushed into the countersink of the drill passage 42a.

Figure 11:
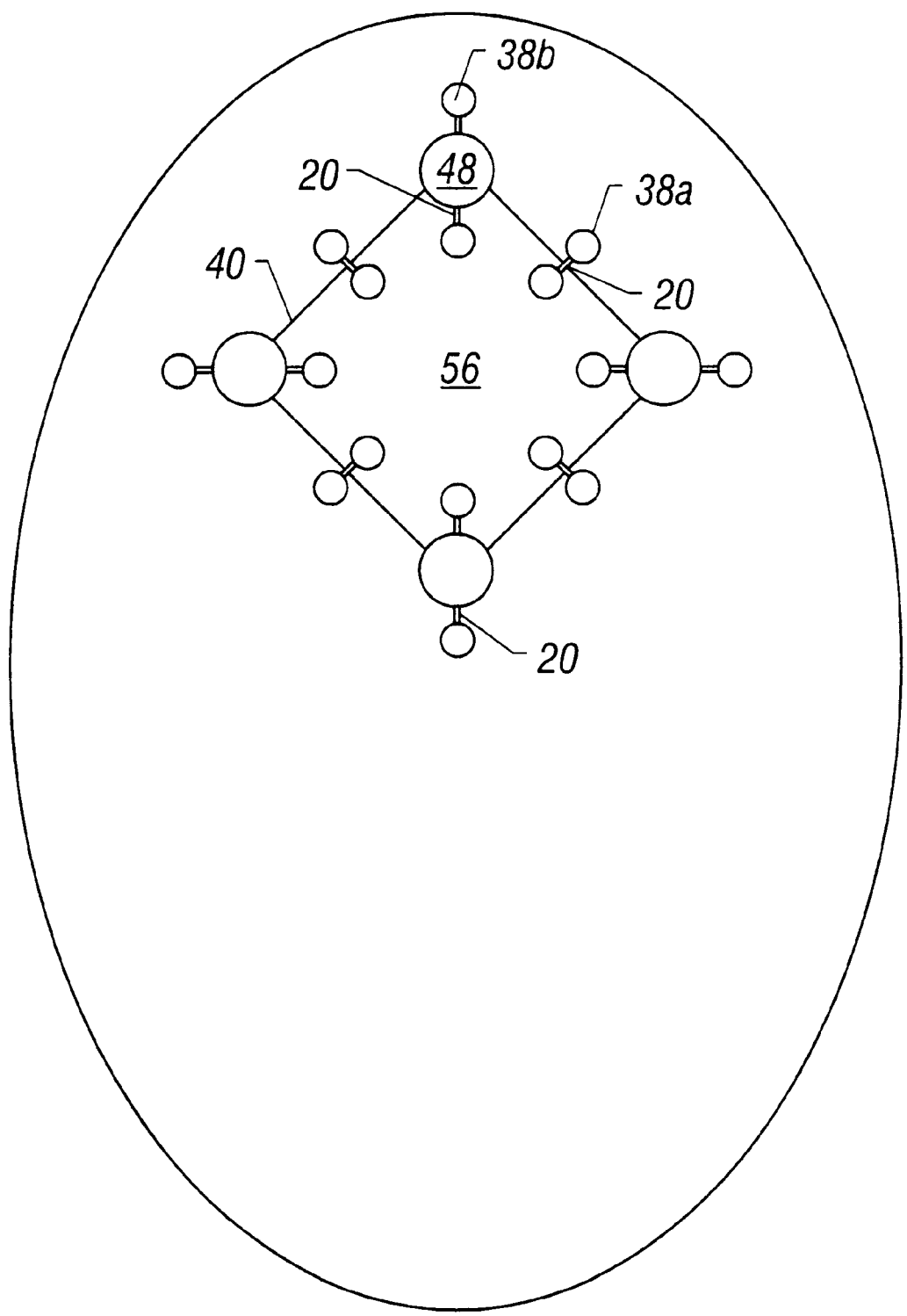
FIG. 11 is a top plan view of one embodiment of the present invention showing the method of attachment of a skull flap to the skull.

As shown in FIG. 11, the skull flap 56 may be secured to the rest of the skull 34 in an expeditious fashion using the quick connection capabilities of the fastener 20 to connect the drill holes 33a and 38b. The fastener 20 may also facilitate the securement of the plates 48 over the burr holes 36. In an embodiment where a portion of the fastener 20 is simply fed through an opposed portion and pulled tight, it is relatively easy to quickly obtain the desired tension in the fastener to connect the bone sections. All of the connections can be concealed in the skull so that when the skin is positioned over the skull 34, no bumps or protrusions remain which could extend through the scalp.

While the present invention has been described with respect to a limited number of preferred embodiments, those skilled in the art will appreciate numerous modifications and variations. It is intended that the appended claims cover all such modifications and variations as fall within the true spirit and scope of the present claims.

What is claimed is:

1. A method for fastening a skull bone section to the skull comprising:

forming an aperture through each of said skull bone section and said skull;

threading a wire having a substantially circular cross-section and having opposed ends through the apertures in each of the skull bone section and said skull; and connecting the wire ends in a self-locking connection using a plurality of serrations on each of said wire ends.

2. The method of claim 1 including adjusting the tension in the wire.

3. The method of claim 2 including threading one of the ends through the other of the ends to form a self-locking connection.

4. The method of claim 1 including connecting a plate to the wire and using the wire to secure the plate over a hole in a bone section.

5. The method of claim 1 including adjusting the wire tension by pulling one end relative to the other end.

* * * * *